US012064286B2

(12) United States Patent
Jiang et al.

(10) Patent No.: US 12,064,286 B2
(45) Date of Patent: Aug. 20, 2024

(54) IMAGE DISPLAY METHOD AND ULTRASOUND IMAGING SYSTEM

(71) Applicant: GE Precision Healthcare LLC, Wauwatosa, WI (US)

(72) Inventors: Zhiqiang Jiang, Wuxi (CN); Jiajiu Yang, Wuxi (CN); Lei Liu, Wuxi (CN); Hujie Jiang, Wuxi (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 378 days.

(21) Appl. No.: 17/391,760

(22) Filed: Aug. 2, 2021

(65) Prior Publication Data

US 2022/0035016 A1 Feb. 3, 2022

(30) Foreign Application Priority Data

Aug. 3, 2020 (CN) .......................... 202010768385.1

(51) Int. Cl.
*A61B 8/00* (2006.01)
*G06T 15/00* (2011.01)
*G06T 15/08* (2011.01)
*G06T 19/00* (2011.01)

(52) U.S. Cl.
CPC .............. *A61B 8/468* (2013.01); *A61B 8/466* (2013.01); *G06T 15/00* (2013.01); *G06T 15/08* (2013.01); *G06T 19/003* (2013.01); *G06T 2207/10136* (2013.01); *G06T 2219/004* (2013.01)

(58) Field of Classification Search
None
See application file for complete search history.

(56) References Cited

U.S. PATENT DOCUMENTS

| 6,370,413 | B1* | 4/2002 | Alvarez | G06T 15/10 600/407 |
| 7,044,912 | B2* | 5/2006 | Babu | A61B 8/483 600/437 |
| 11,521,345 | B2* | 12/2022 | Jiang | G01S 7/52084 |
| 2005/0049500 | A1* | 3/2005 | Babu | G06T 19/00 600/443 |
| 2007/0255139 | A1 | 11/2007 | Deschinger | |
| 2012/0050278 | A1 | 3/2012 | Iizuka | |
| 2022/0035016 | A1* | 2/2022 | Jiang | G01S 7/52084 |

FOREIGN PATENT DOCUMENTS

| CN | 101061962 B | 1/2012 |
| CN | 102415895 B | 9/2014 |

OTHER PUBLICATIONS

CN application 202010768385.1 filed Aug. 3, 2020—office action issued Sep. 12, 2023; 7 pages.

* cited by examiner

*Primary Examiner* — Tahmina N Ansari (57) ABSTRACT

The present application provides an image display method and an ultrasound imaging system. The image display method includes performing a position adjustment operation on an initial volume view in an image display interface to obtain at least one reference volume view, storing position information of the at least one reference volume view, and creating at least one label to point to the position information, the at least one label being displayed in the image display interface.

11 Claims, 5 Drawing Sheets

IMAGE DISPLAY METHOD AND ULTRASOUND IMAGING SYSTEM

TECHNICAL FIELD

The present invention relates to the field of ultrasound detection, and more specifically relates to an image display method and an ultrasound imaging system.

BACKGROUND

Ultrasound imaging is a medical imaging technique for imaging organs and soft tissues in the human body. Ultrasound imaging uses real-time and non-invasive high-frequency sound waves to produce two-dimensional (2D) images, three-dimensional (3D) images, and/or four-dimensional (4D) images (i.e., real-time/continuous 3D images).

Ultrasound imaging is a valuable non-intrusive tool for diagnosing various medical conditions. Acquired ultrasound data can be analyzed and/or processed to thereby enable a user (e.g., a medical professional) to perform evaluation on an anatomical structure under test and conduct a diagnosis. In the case where an ultrasound image is a volume rendering of 3D image data or 4D image data, the user can rotate an object depicted in the volume rendering to obtain a desired view, but this process is quite cumbersome and time-consuming. In an actual operation process, the user may need to repeatedly or repetitively inspect a certain view, and how to return to a certain view or repetitively inspect a view is a big challenge.

In existing solutions, original data in different directions can be stored to implement repetitive inspection. However, the original data is relatively large in volume, and will occupy a large amount of memory, and import and/or export of the data is also quite time-consuming.

In addition, 2D images of views in different directions may also be saved (for example, in the form of screenshots) to implement repetitive inspection. However, since this method captures and stores 2D images, parameters or views are adjustable, rendering the method quite inconvenient.

In addition, an operation process can also be replayed by recording all operations of the user, so as to implement repetitive inspection. However, there are certain problems in replaying operation records. The user cannot jump to any views at will, but can only replay views in accordance with the operation process. Moreover, when operating from a target view to a desired view, the user may go through various repetitive or cumbersome operation processes, and replaying these records will be futile and time-consuming.

BRIEF DESCRIPTION

According to an embodiment, an image display method includes performing a position adjustment operation on an initial volume view in an image display interface to obtain at least one reference volume view. The method includes storing position information of the at least one reference volume view and creating at least one label to point to the position information. The at least one label is displayed in the image display interface.

According to an embodiment, an ultrasound imaging system includes a processor including a position adjustment module configured to perform a position adjustment operation on an initial volume view to obtain at least one reference volume view. The processor includes a label creation module configured to store position information of the at least one reference volume view and create at least one label to point to the position information. The ultrasound imaging system also includes an image display interface configured to display the initial volume view, the at least one reference volume view an the at least one label.

According to an embodiment, a non-transitory, computer-readable storage medium is configured to store a computer program that, when executed by a computer, causes the computer to perform a position adjustment operation on an initial volume view in an image display interface to obtain at least one reference volume view, store position information of the at least one reference volume view, and create at least one label to point to the position information, wherein the at least one label is displayed in the image display interface.

BRIEF DESCRIPTION OF THE DRAWINGS

The present invention may be better understood by describing exemplary embodiments of the present invention with reference to accompanying drawings, in which.

DETAILED DESCRIPTION

Specific embodiments of the present invention will be described in the following. It should be noted that during the specific description of the embodiments, it is impossible to describe all features of the actual embodiments in detail in this description for the sake of brief description. It should be understood that in the actual implementation of any of the embodiments, as in the process of any engineering project or design project, a variety of specific decisions are often made in order to achieve the developer's specific objectives and meet system-related or business-related restrictions, which will vary from one embodiment to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The terms "first," "second," and similar terms used in the description and claims of the patent application of the present invention do not denote any order, quantity, or importance, but are merely intended to distinguish between different constituents. "One," "a(n)," and similar terms are not meant to be limiting, but rather denote the presence of at least one. The term "include," "comprise," or a similar term is intended to mean that an element or article that appears before "include" or "comprise" encompasses an element or article and equivalent elements that are listed after "include" or "comprise," and does not exclude other elements or articles. The term "connect," "connected," or a similar term is not limited to a physical or mechanical connection, and is not limited to a direct or indirect connection.

The term "image" broadly refers to a visual image and data representing the visual image. However, many embodiments generate (or are configured to generate) at least one visual image. In addition, as used herein, the phrase "image" is used to refer to an ultrasound mode, such as a B mode (2D mode), an M mode, a three-dimensional (3D) mode, a CF mode, PW Doppler, CW Doppler, MGD, and/or a B sub-mode and/or a CF sub-mode, such as shear wave elasticity imaging (SWEI), TVI, angiography (Angio), gray-scale blood flow (B-flow), BMI, and BMI angiography (BMI-Angio), and in some cases, MM, CM, and TVD, where "image" and/or "plane" includes a single beam or a plurality of beams.

Figure 1:
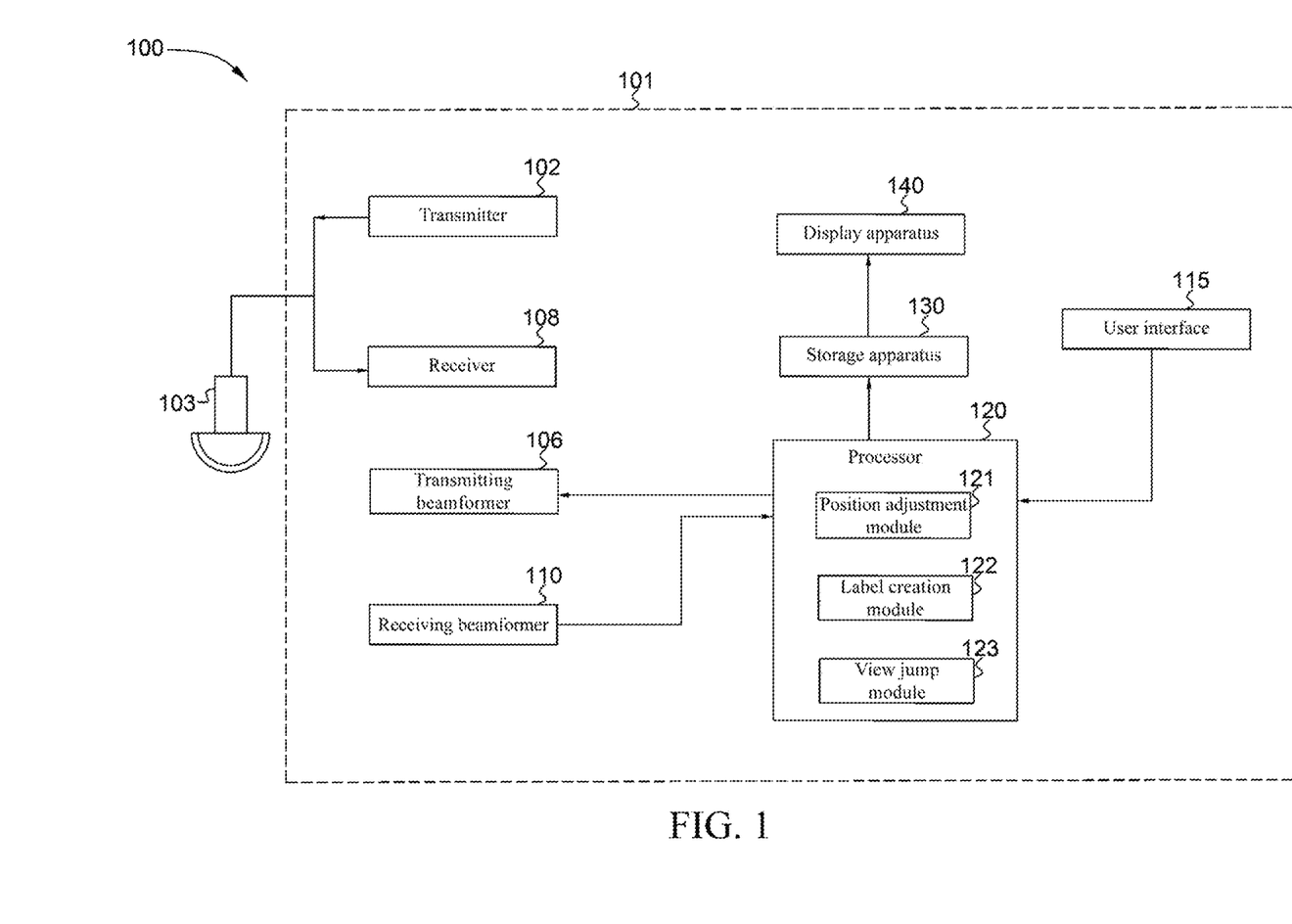
FIG. 1 is a schematic diagram of an ultrasound imaging system according to an embodiment of the present invention.

FIG. 1 shows an ultrasound imaging system 100 according to some embodiments of the present invention. As shown in FIG. 1, the ultrasound imaging system 100 comprises an ultrasound imaging apparatus 101 and a probe 103. The ultrasound imaging apparatus 101 may have different sizes and/or shapes. For example, the ultrasound imaging apparatus may be a cart-based ultrasound imaging apparatus, or a laptop computer-type ultrasound imaging apparatus, or a handheld ultrasound imaging apparatus.

The ultrasound imaging apparatus 101 includes a transmitting beamformer 106, a transmitter 102, a receiver 108 and a receiving beamformer 110. The transmitting beamformer 106 and the transmitter 102 drive (an internal element, e.g. a piezoelectric element, of) the probe 103 to transmit a pulsed ultrasound signal to an object under detection (not shown). The pulsed ultrasound signal is backscattered from a structure (like blood cells or muscle tissue) in the body to generate an echo that returns to the probe 103. The echo is converted into an electrical signal or ultrasound data by the probe 103, and the receiver 108 receives the electrical signal. The electrical signal representing the received echo passes through the receiving beamformer 110 that outputs ultrasound data.

According to some embodiments, the probe 103 may comprise an electronic circuit system to perform all or part of the transmitting and/or receiving beamforming. For example, all or part of the transmitting beamformer 106, the transmitter 102, the receiver 108 and the receiving beamformer 110 may be located in the probe 103. In addition, the probe 103 may be either a 2D array probe, or a 3D or 4D array probe. The term "scan/scanning" may also be used to refer to acquiring data during the process of transmitting or receiving ultrasound signals, the data covering at least most of anatomical structures (such as the heart, blood vessels, or any suitable anatomical structure). The term "data" or "ultrasound data" may be used to refer to one or more data sets acquired by an ultrasound imaging system.

The ultrasound imaging apparatus 100 further includes a processor 120, so as to control the transmitting beamformer 106, the transmitter 102, the receiver 108, and the receiving beamformer 110. The processor 120 is communicatively connected to the probe 103.

Specifically, the processor 120 can control the shape of a beam transmitted from the probe 103, acquire data from the probe 103, process acquired ultrasound information (e.g., RF signal data or IQ data pairs), and prepare a frame of the ultrasound information to display the ultrasound information on a display apparatus 140. The term "communicatively connected" includes wired and wireless connection. In some embodiments, the processor 120 may also include a complex demodulator (not shown) configured to demodulate RF data and generate original data.

Specifically, the processor 120 may include a central processing unit (CPU). Optionally, the processor 120 may include other electronic components capable of executing processing functions, such as digital signal processors, field programmable gate arrays (FPGA), or graphic boards. In some embodiments, the processor 120 may include a plurality of electronic components capable of executing processing functions. For example, the processor 120 may include two or more electronic components selected from an electronic component list. The electronic component list includes: a CPU, a digital signal processor, a field programmable gate array, and a graphic board.

The ultrasound imaging apparatus 100 further includes a storage apparatus 130 for storing acquired data (or data sets) and/or images. For example, the storage apparatus 130 may include a hard disk drive, a floppy disk drive, a CD-read/write (CD-R/W) drive, a digital versatile disc (DVD) drive, a flash drive, and/or a solid-state storage apparatus.

The ultrasound imaging apparatus 100 further includes the display apparatus 140. The display apparatus 140 includes one or a plurality of monitors that display patient information including diagnostic ultrasound images to the user for diagnosis and analysis. The display apparatus 140 is communicatively connected to the processor 120.

The ultrasound imaging apparatus 100 further includes a user interface 115. The user interface 115 can be used to control the operation of the ultrasound imaging system 100, including controlling the input of patient data, changing scan or display parameters, etc. The user interface 115 may include a button (or a plurality of buttons), a rotary encoder (or a plurality of rotary encoders), a touch screen, a touch pad, a trackball, a motion tracking device, a voice recognition device, a mouse device, a keyboard, a camera, and/or any other device capable of receiving user instructions.

In various embodiments of the present invention, data can be processed by other or different mode-related modules of the processor 120 (for example, B-mode, color Doppler, M-mode, color M-mode, spectral Doppler, elastography, tissue velocity imaging (TVI), strain imaging, strain rate imaging, etc.) to form 2D or 3D or 4D data. For example, one or a plurality of modules can generate B-mode, color Doppler, M-mode, color M-mode, spectral Doppler, elastography, TVI, strain imaging, strain rate imaging and combinations thereof, etc.

It should be noted that various embodiments can be described in conjunction with an ultrasound system, but methods and systems are not limited to ultrasound imaging or its specific configuration. Various embodiments can be implemented in conjunction with different types of imaging systems, including, for example, multi-modality imaging systems having ultrasound imaging systems and one of x-ray imaging systems, magnetic resonance imaging (MM) systems, computed tomography (CT) imaging systems, positron emission tomography (PET) imaging systems, among others. In addition, various embodiments can be implemented in non-medical imaging systems, for example, non-destructive detection systems such as ultrasound weld detection systems or airport baggage scanning systems.

Generally, the processor 120 may include appropriate logic, circuitry, interfaces, and/or code, and the appropriate logic, circuitry, interface, and/or code may be operable to process ultrasound scan data to generate an ultrasound image for presentation on the display apparatus 140. The display apparatus 140 may include an image display interface for displaying the ultrasound image, and the user may perform at least one operation on the ultrasound image on the basis of the user interface 115, so as to change the position or direction or the like of the ultrasound image, and display the ultrasound image in the image display interface.

In some embodiments, the processor 120 includes a position adjustment module 121 and a label creation module 122. The position adjustment module 121 is configured to perform a position adjustment operation on an initial volume view to obtain at least one reference volume view. The label creation module 122 is configured to store position information of the at least one reference volume view, and create at least one label to point to the position information. The display apparatus 140 includes an image display interface for displaying the initial volume view, the at least one reference volume view, and the at least one label.

Specifically, the initial volume view is a volume rendering generated from an ultrasound three-dimensional or four-dimensional volume. Specifically, the at least one reference volume view obtained after the position adjustment operation on the initial volume view is also a volume rendering generated from an ultrasound three-dimensional or four-dimensional volume.

Figure 2:
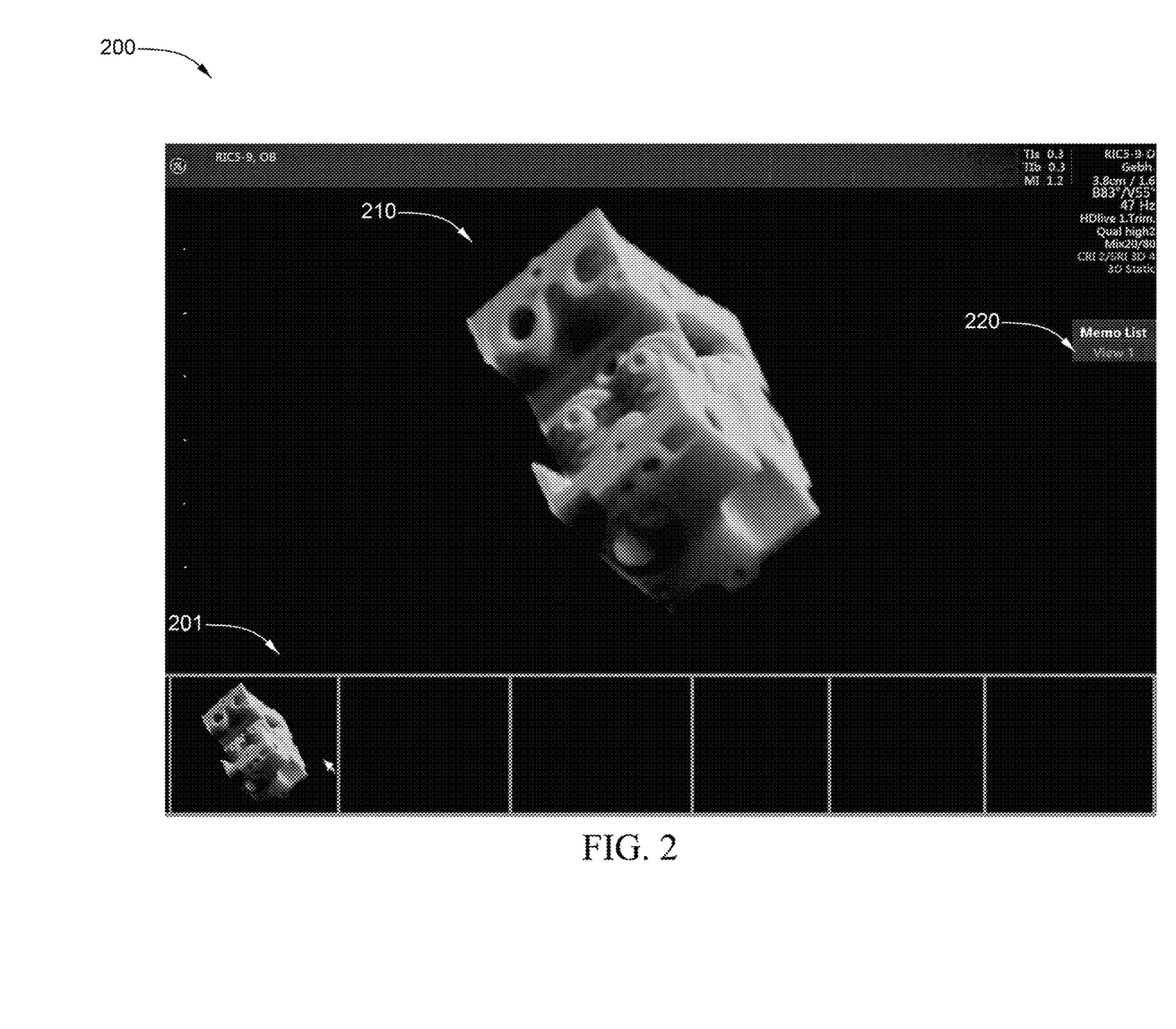
FIG. 2 illustrates a first image display interface for a first reference volume view and a first label.

FIG. 2 shows a first image display interface for a first reference volume view and a first label. As shown in FIG. 2, an image display interface 200 may display an initial volume view 201. The position adjustment module 121 may perform a first set of position adjustment operations on the initial volume view 201 to obtain a first reference volume view 210. The label creation module 122 can store position information of the first reference volume view 210 on the basis of a user input (such as a key or button press on a control panel of the ultrasound imaging system, a mouse click, or a touch on an option in the image display interface), and create a first label (View 1) 220 to point to the position information.

Although the first reference volume view 210 is obtained by performing the position adjustment operation on the initial volume view 201, those skilled in the art should understand that it is also possible to directly store the position information of the initial volume view without performing the position adjustment operation on the initial volume view, and create the first label to point to the position information, so as to facilitate repetitive or repeated inspection of the initial volume view.

Although FIG. 2 shows that the first label is shown in the form of "View 1," those skilled in the art should understand that the first label may also be displayed as any other text, number, or graph, for example, "First label" or "1st label" or "View I", etc. More optimally, the first label may be displayed in the form of a thumbnail of the view, so as to display the view in the image display interface in a clearer manner. After the label is created, when a user moves the mouse to the label but does not click on the label, the image display interface may also be configured to display a thumbnail, a screenshot, etc. of the view corresponding to the label by means of a small window, so as to prompt the user before clicking.

Figure 3:
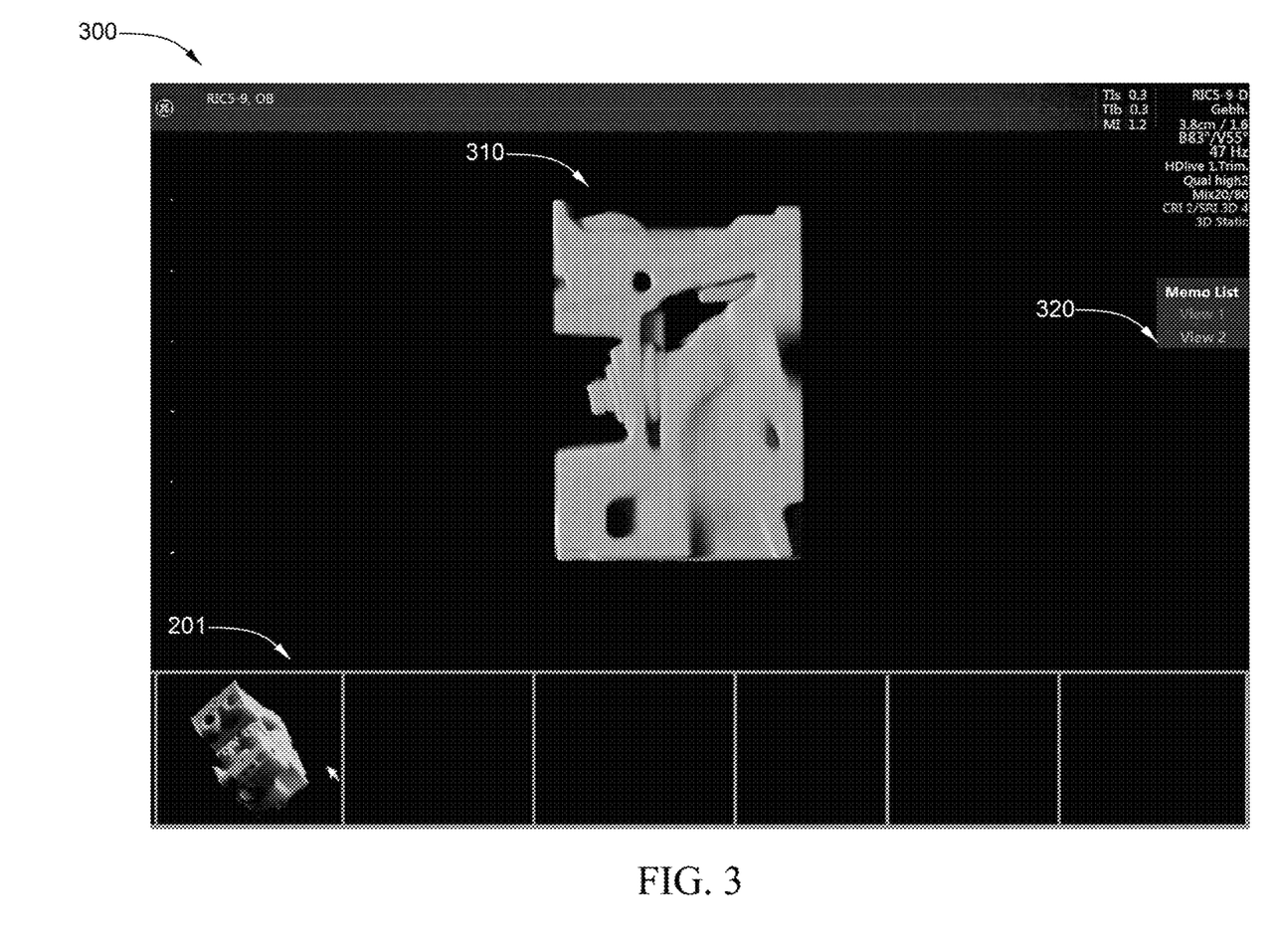
FIG. 3 illustrates a second image display interface for a second reference volume view and a second label.

FIG. 3 shows a second image display interface for a second reference volume view and a second label. As shown in FIG. 3, in an image display interface 300, the position adjustment module 121 may perform a second set of position adjustment operations on the first reference volume view 210 to obtain a second reference volume view 310, and the label creation module 122 may store position information of the reference volume view 310, and create a second label 320 to point to the position information.

Figure 4:
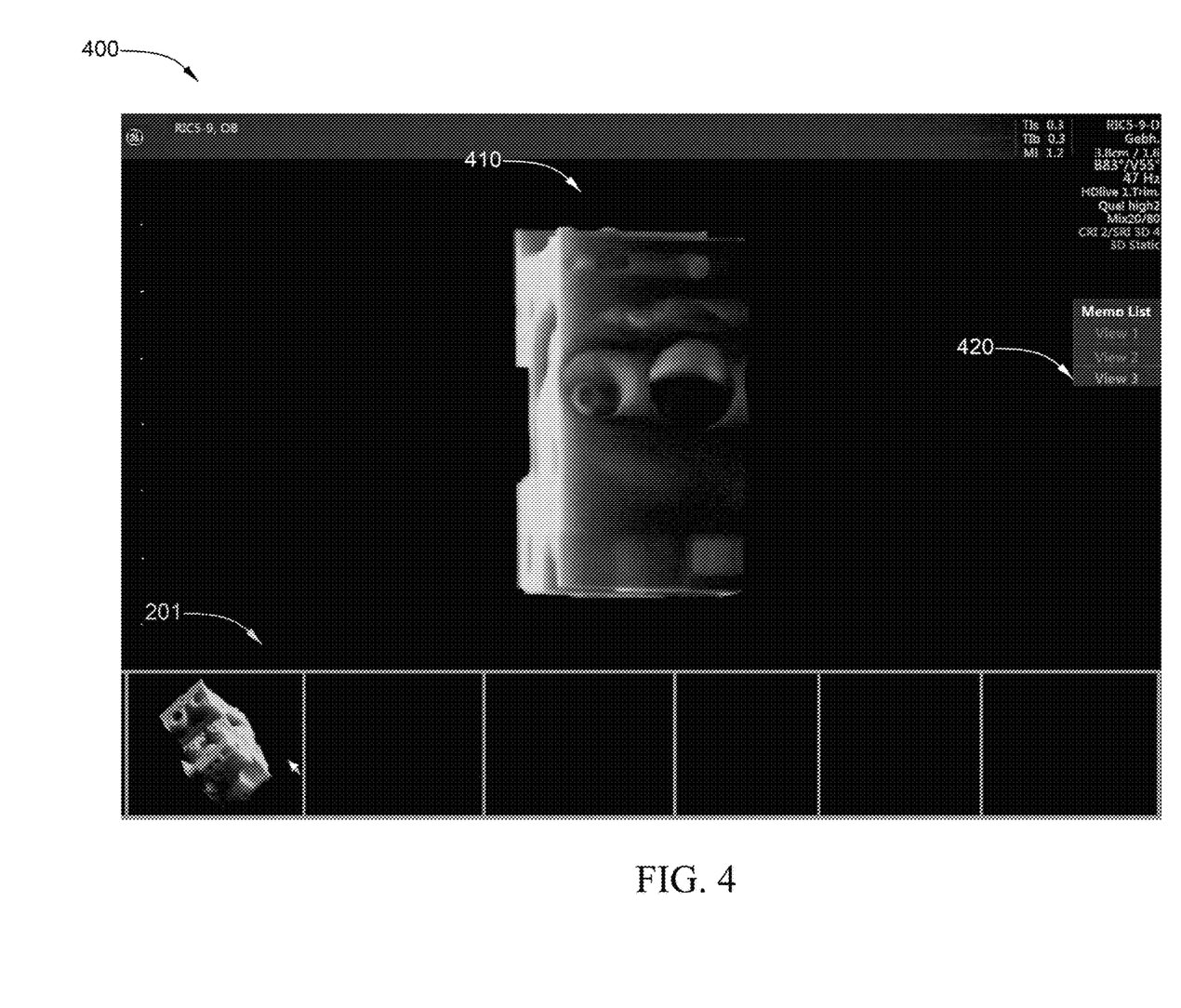
FIG. 4 illustrates a third image display interface for a third reference volume view and a third label.

FIG. 4 shows a third image display interface for a third reference volume view and a third label. As shown in FIG. 4, in an image display interface 400, the position adjustment module 121 may perform a third set of position adjustment operations on the second reference volume view 310 to obtain a third reference volume view 410, and the label creation module 122 may store position information of the third reference volume view 410, and create a third label 420 to point to the position information.

Although FIGS. 2-4 show the initial volume view 201 at the bottom of the image display interface, those skilled in the art should be aware that such display is not necessary, and that the initial volume view may be not displayed. In addition to showing one set of initial volume views 201, a plurality of sets of different initial volume views may also be shown together with the initial volume view.

In some embodiments, the aforementioned position adjustment operation includes at least one of rotation in at least one direction and movement in at least one direction, for example, rotation to the right by 15 degrees. Those skilled in the art should understand that a position adjustment operation on a certain view may include a plurality of operating processes, and the plurality of operating processes may also be repeated or overlapped, for example, rotation to the right by 15 degrees followed by rotation to the left by 10 degrees.

In some embodiments, the position information includes a coordinate position, wherein the origin of the coordinate position is position information of the initial volume view. Specifically, the position of the initial volume view is an initial placement position of the probe.

The processor 120 may further include a view jump module 123, which is configured to operate one of the at least one label to display a corresponding reference volume view.

Specifically, for example, if the image display interface currently displays the third reference volume view 410 as shown in FIG. 4, when the user performs an operation on (clicks the mouse or touches on) the first label 220 (shown as View 1), the image display interface will jump to display the first reference volume view 210. Similarly, when the user operates the second label 320 (shown as View 2), the image display interface will jump to display the second reference volume view 310.

Certainly, if the second reference volume view 310 as shown in FIG. 3 is currently displayed, when the user operates the first label, the image display interface will jump to display the first reference volume view 210. Similarly, when the user operates the third label 420, the image display interface will jump to display the third reference volume view 410.

In addition, if the first reference volume view 210 is currently displayed, when the user operates the second label 320, the image display interface will display the second reference volume view 310. Similarly, when the user operates the third label 420, the image display interface will display the third reference volume view 410.

In a process of view jumping, the size, color, etc. of a label may be changed to identify or highlight the label corresponding to a current view, so as to prompt a subsequent view jump or label operation.

Although the present invention only provides three labels and three reference volume views, those skilled in the art should understand that any number of labels may be created in actual use, and any label may be clicked on to jump to and display a corresponding reference volume view, which is not necessarily displayed in order.

In some embodiments, the view jump module 130 is further configured to operate one of at least one label to display a dynamic process of jumping from a current view to a corresponding reference volume view. Specifically, for example, if the image display interface currently displays the third reference volume view 410, when the user operates the first label 220, the image display interface will display a dynamic process of jumping from the current view (i.e., the third reference volume view 410) to the first reference volume view 210 (i.e., a desired view) corresponding to the first label 220, and then statically display the first reference volume view 210.

In some embodiments, the view jump module 130 is further configured to calculate a shortest path between position information of the current view and position information of the corresponding reference volume view, and display, on the basis of the shortest path, a dynamic process of jumping from the current view to the corresponding reference volume view.

Specifically, if the image display interface currently displays the third reference volume view 410 as shown in FIG. 4, when the user operates the second label 320 (shown as View 2), the image display interface will display a dynamic process of taking a shortest path to jump from the current view (the third reference volume view 410) to the second reference volume view 310 corresponding to the second label 320. For example, if the second reference volume view 310 is first rotated to the left by 45 degrees, and then rotated to the right by 30 degrees to obtain the third reference volume view 410, then the view jump module 130 may calculate a shortest path between position information (coordinate position) of the second reference volume view 310 and position information (coordinate position) of the third reference volume view 410, that is, only rotation to the left by 15 degrees needs to be performed. Therefore, the image display interface will display a dynamic process of rotating the current view (the third reference volume view 410) to the right by 15 degrees to obtain the second reference volume view 310, and finally statically display the second reference volume view 310 without replaying the entire operation process. That is, the user is provided with a dynamic display process to intuitively inspect a view, and the dynamic process can be simplified and time be saved.

Figure 5:
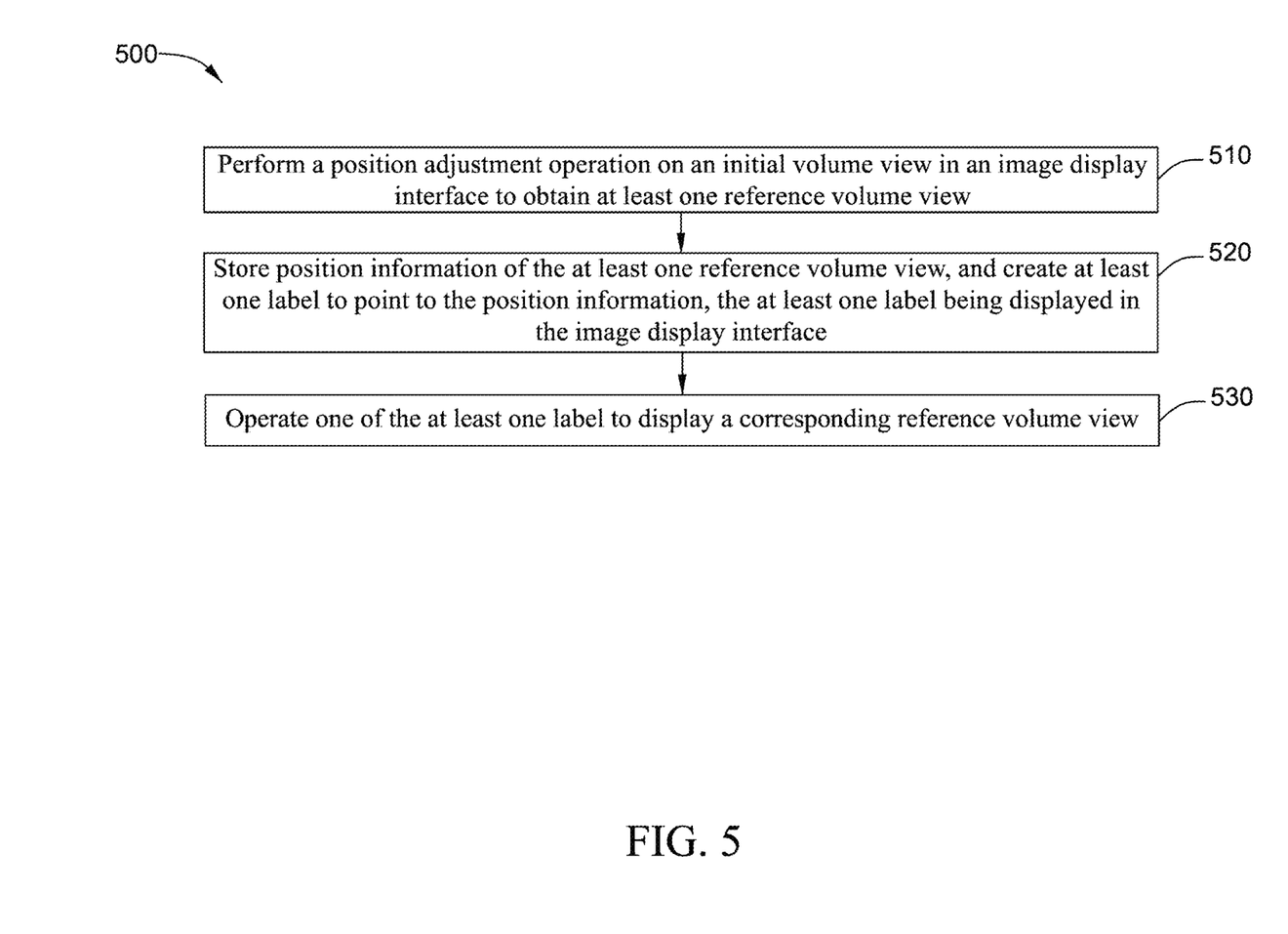
FIG. 5 is a flowchart of an image display method according to some embodiments of the present invention.

FIG. 5 shows a flowchart of an image display method 500 according to some embodiments of the present invention. As shown in FIG. 5, the image display method 500 according to some embodiments of the present invention includes step 510 and step 520.

At step 510, a position adjustment operation is performed on an initial volume view in an image display interface to obtain at least one reference volume view.

Specifically, the initial volume view is a volume rendering generated from an ultrasound three-dimensional or four-dimensional volume. Correspondingly, at least one reference volume view is also a volume rendering generated from an ultrasound three-dimensional or four-dimensional volume.

Specifically, the position adjustment operation may include at least one of a rotation in at least one direction or a movement in at least one direction.

At step 520, position information of the at least one reference volume view is stored, and at least one label is created to point to the position information, the at least one label being displayed in the image display interface.

Specifically, the position information includes a coordinate position, wherein the origin of the coordinate position is position information of the initial volume view.

In addition to storing the position information of the at least one reference volume view and creating the label, storing the position information of the initial volume view and creating a label to point to the position information can also be performed.

Specifically, a first set of position adjustment operations are performed on the initial volume view to obtain a first reference volume view, position information of the first reference volume view is stored, and a first label is created to point to the position information; a second set of position adjustment operations are performed on the first reference volume view to obtain a second reference volume view, position information of the second reference volume view is stored, and a second label is created to point to the position information; and a third set of position adjustment operations are performed on the second reference volume view to obtain a third reference volume view, position information of the third reference volume view is stored, and a third label is created to point to the position information. Specifically, at least one of the initial volume view, the first reference volume view, the second reference volume view, the third reference volume view, the first label, the second label, and the third label may be displayed in the image display interface.

In some embodiments, the image display method 500 further includes step 530.

At step 530, one of the at least one label is operated to display a corresponding reference volume view.

Specifically, the displaying a corresponding reference volume view includes operating one of at least one label to display a dynamic process of jumping from a current view to a corresponding reference volume view.

Specifically, the displaying a dynamic process of jumping from a current view to a corresponding reference volume view includes: calculating a shortest path between position information of the current view and position information of the corresponding reference volume view, and displaying, on the basis of the shortest path, a dynamic process of jumping from the current view to the corresponding reference volume view. In the process of performing a position adjustment operation on the initial volume view, a user may have to perform various cumbersome and repetitive operations to obtain a desired reference volume view. By expecting a shortest path between position information of the current view and position information of the desired view, the user can perform rotation and/or movement on the basis of the shortest path, so that a dynamic process of jumping from the current view to the desired view can be dynamically displayed. This not only saves time, but also displays a clear and simple process, thereby providing the user with intuitive visual effects.

Specifically, if the first reference volume view 210 is currently displayed, by operating the second label 320, the user may be displayed a dynamic process of jumping from the first reference volume view 210 to the second reference volume view 310, and the second reference volume view 310 may be statically displayed; and by operating the third label 420, the user may be displayed a dynamic process of jumping from the first reference volume view 210 to the third reference volume view 410, and the third reference volume view 410 may be statically displayed.

If the second reference volume view 310 is currently displayed, by operating the first label 220, the user may be displayed a dynamic process of jumping from the second reference volume view 310 to the first reference volume view 210, and the first reference volume view 210 may be statically displayed; and by operating the third label 420, the user may be displayed a dynamic process of jumping from the first reference volume view 210 to the third reference volume view 410, and the third reference volume view 410 may be statically displayed.

If the third reference volume view 410 is currently displayed, by operating the first label 220, the user may be displayed a dynamic process of jumping from the third reference volume view 410 to the first reference volume view 210, and the first reference volume view 210 may be statically displayed; and by operating the second label 320, the user may be displayed a dynamic process of jumping from the third reference volume view 410 to the second reference volume view 310, and the second reference volume view 310 may be statically displayed.

In the image display method proposed by the present invention, by means of storing position information of a desired view and creating a label to point to the position information, the label may correspond to coordinate position of the desired view in an one-to-one manner, thereby enabling a user to jump between views easily, and no restriction is imposed on the order or sequence of views inspected. Moreover, unlike saved screenshots, the view is also editable. In addition, storing the position information does not require a large amount of storage space, and the time required for data import/export is also saved. By means of a configuration of dynamically displaying a dynamic operation process of jumping from a current view to a desired view, a user may be provided with intuitive dynamic effects. By means of a configuration of a shortest path dynamically displayed, the operation time required for the user can be saved, and the entire operation process does not need to be repeated.

The present invention may further provide a non-transitory computer-readable storage medium, which is configured to store an instruction set and/or a computer program. When executed by a computer, the instruction set and/or computer program causes the computer to perform the foregoing method for obtaining a predicted image of a truncated portion. The computer executing the instruction set and/or computer program may be a computer of an ultrasound imaging system, or may be another apparatus/module of the ultrasound imaging system. In one embodiment, the instruction set and/or computer program may be programmed in a processor/controller of the computer.

Specifically, when executed by the computer, the instruction set and/or computer program causes the computer to:

perform a position adjustment operation on an initial volume view in an image display interface to obtain at least one reference volume view; and store position information of the at least one reference volume view, and create at least one label to point to the position information, the at least one label being displayed in the image display interface.

The instructions described above may be combined into one instruction for execution, and any of the instructions may also be split into a plurality of instructions for execution. Moreover, the present invention is not limited to the instruction execution order described above.

As used herein, the term "computer" may include any processor-based or microprocessor-based system including a system that uses a microcontroller, a reduced instruction set computer (RISC), an application specific integrated circuit (ASIC), a logic circuit, and any other circuit or processor capable of executing the functions described herein. The above examples are merely exemplary and thus are not intended to limit the definition and/or meaning of the term "computer" in any manner.

The instruction set may include various commands that instruct a computer acting as a processor or instruct a processor to perform particular operations, such as the methods and processes of various embodiments. The instruction set may be in the form of a software program, and the software program can form part of one or a plurality of tangible, non-transitory computer-readable media. The software may be in various forms such as system software or application software. In addition, the software may be in the form of a set of independent programs or modules, a program module within a larger program, or part of a program module. The software may also include modular programming in the form of object-oriented programming. The input data may be processed by the processor in response to an operator command, or in response to a previous processing result, or in response to a request made by another processor.

Some exemplary embodiments have been described above; however, it should be understood that various modifications may be made. For example, if the described techniques are performed in a different order and/or if the components of the described system, architecture, apparatus, or circuit are combined in other manners and/or replaced or supplemented with additional components or equivalents thereof, a suitable result can be achieved. Accordingly, other implementations also fall within the protection scope of the claims.

The invention claimed is:

1. An image display method, comprising:
performing a position adjustment operation on an initial volume view in an image display interface to obtain at least one reference volume view; and
storing position information of the at least one reference volume view; and
creating at least one label to point to the position information, the at least one label being displayed in the image display interface,
further comprising:
operating one of the at least one label to display a corresponding reference volume view, wherein the displaying a corresponding reference volume view comprises:
operating one of the at least one label to display a dynamic process of jumping from a current view to a corresponding reference volume view.

2. The image display method according to claim 1, wherein the displaying a dynamic process of jumping from a current view to a corresponding reference volume view comprises:
calculating a shortest path between position information of the current view and position information of the corresponding reference volume view; and
displaying, on the basis of the shortest path, a dynamic process of jumping from the current view to the corresponding reference volume view.

3. The image display method according to claim 1, wherein the position adjustment operation comprises at least one of rotation in at least one direction or movement in at least one direction.

4. The image display method according to claim 1, wherein the position information comprises a coordinate position, and wherein the origin of the coordinate position is position information of the initial volume view.

5. The image display method according to claim 1, wherein the initial volume view is a volume rendering generated from an ultrasound three-dimensional or four-dimensional volume.

6. An ultrasound imaging system, comprising:
a memory storing instructions; and
a processor configured to execute the instructions to:
perform a position adjustment operation on an initial view of a three-dimensional (3D) volume rendering to obtain at least one reference view of the 3D volume rendering; and
store position information of the at least one reference view
create at least one label to point to the position information;
control a display to display the initial view and the at least one label; and
responsive to a selection of one of the at least one label, control the display to display a corresponding reference view by controlling the display to display a dynamic process of jumping from a current view to the corresponding reference view.

7. The ultrasound imaging system according to claim 6, wherein the view jump module is further configured to:
calculating a shortest path between position information of the current view and position information of the corresponding reference view; and
displaying a dynamic process of jumping from the current view to the corresponding reference view based on the shortest path.

8. A non-transitory computer-readable storage medium, configured to store a computer program that, when executed by a computer, causes the computer to:
perform a position adjustment operation on an initial volume view of a three-dimensional (3D) volume rendering in an image display interface to obtain at least one reference view of the 3D volume rendering;
store position information of the at least one reference view; and
create at least one label to point to the position information; control a display to display the at least one label;
responsive to a selection of one of the at least one label, control the display to display a corresponding reference view by controlling the display to display a dynamic process of jumping from a current view to the corresponding reference view.

9. The non-transitory computer-readable storage medium of claim claim 8, wherein displaying the dynamic process of jumping from the current view to the corresponding reference view comprises:
calculating a shortest path between position information of the current view and position information of the corresponding reference view; and
displaying a dynamic process of jumping from the current view to the corresponding reference volume view based on the shortest path.

10. The non-transitory computer-readable storage medium of claim 8, wherein the position adjustment operation comprises at least one of a rotation in at least one direction or a movement in at least one direction.

11. The non-transitory computer-readable storage medium of claim 8, wherein the initial view is a volume rendering generated from an ultrasound three-dimensional or four-dimensional volume.

\* \* \* \* \*